United States Patent [19]

Johnson

[11] Patent Number: 4,504,963
[45] Date of Patent: Mar. 12, 1985

[54] AUTOMATICALLY CALIBRATING MEAT ANALYSIS DEVICE

[76] Inventor: Lloyd D. Johnson, 2850 Cedar St., Davenport, Iowa 52804

[21] Appl. No.: 484,873

[22] Filed: Apr. 14, 1983

[51] Int. Cl.³ ............................................. G01N 23/00
[52] U.S. Cl. .................................... 378/53; 364/556; 378/98; 378/207
[58] Field of Search ............................ 378/53, 207, 98; 364/568, 556

[56] References Cited

U.S. PATENT DOCUMENTS

2,992,332  7/1961  Madigan ............................... 378/53
4,168,431  9/1979  Henriksen ............................ 378/53

Primary Examiner—Alfred E. Smith
Assistant Examiner—T. N. Grigsby
Attorney, Agent, or Firm—Lockwood, Alex, Fitzgibbon & Cummings

[57] ABSTRACT

An apparatus, system and method are provided for determining the percentage of fat in a meat sample through the use of X-ray radiation techniques. An automatic calibration feature eliminates the need for manual potentiometer adjustments for accommodating interaction between X-ray attenuation by pairs of calibration standards of known fat percentage values for a given meat species. Protein and moisture percentages may be determined. Indicators for needed periodic recalibration also may be included, and adjustments may be incorporated for meat samples of high, normal or low moisture content, as well as for different species of meat.

32 Claims, 3 Drawing Figures

AUTOMATICALLY CALIBRATING MEAT ANALYSIS DEVICE

BACKGROUND AND DESCRIPTION OF THE INVENTION

This invention generally relates to determining the fat content of a meat sample, more particularly to determining the fat content by the use of X-ray radiation in such a manner as to automatically calibrate in order to balance X-ray beams as they are attenuated by pairs of simulated meat samples.

In the processing of meat products, there are several occasions when it is important to know exactly the percentage of fat in the meat being processed, and to a lesser extent the percentage of protein and moisture in such meat. Laboratory methods for determining fat percentages have long been known and practiced, which methods typically require a change in the physical or chemical properties of the meat sample, or they otherwise destroy the sample. Additionally, although laboratory analysis techniques typically require from several to 24 hours to complete, they are still practiced because of their accuracy and reliability.

More rapid fat determination is characteristic of devices such as those using X-ray analysis or other techniques. X-ray procedures have the advantage of being both rapid and non-destructive of the meat being analyzed. Known non-destructive means include those shown in U.S. Pat. Nos. 2,992,332, 4,168,431 and 4,171,164. In each of these non-destructive approaches, the operator must manually calibrate the device on a periodic basis in order to maintain the accuracy thereof.

Requiring manual calibration imparts an element of subjectivity that tends to diminish the overall accuracy of these types of devices. Accuracy is an important element that is of substantial economic importance. When fat percentage is measured before meat is ground or otherwise restructured, it is possible to initially prepare products that closely approximate a desired fat content by selection or blending of quantities of meats of differing fat percentages. It is also useful to be able to readily measure the fat content of a product after it has been ground or restructured in order to be able to maintain a certain process control of the product by adjusting the input of fat, protein and moisture into the meat processing system.

In those situations where a meat processing plant attains its meat from a vendor, the price of the meat will vary in proportion to its lean content. Accordingly, it is important to the vendor that the lean content be no higher than the amount specified on the invoice. For the vendor's customers, it is important that they determine that the lean content is no lower than the invoiced amount.

Unless they are carefully calibrated and maintained, X-ray analysis devices are somewhat vulnerable insofar as maintaining their accuracy is concerned due to numerous variables. One important variable is the temperature at the X-ray tube. Generally speaking, the higher the temperature, the greater the number of electrons that are emitted by the tube and directed toward the target in response to a given tube excitation potential. Such temperature changes can be caused by drafts, extensive use, variations in room temperature from time to time throughout the day, and so forth. Such can affect the accuracy of these devices by as much as 2 percent or more, which can be a significant economic difference.

Calibration of these devices also tends to be affected by the number of times that the device is used and the time elapsed since previous calibration. On occasion, when these devices are not properly utilized, decalibration can occur due to movement of the X-ray head with respect to the target. Component parameters can also change, for example, high resistance and high voltage impart significant stresses on the system, the X-ray tube ages, and the feedback resistance from the X-ray tube will change over time of use. When resistance changes as voltage is applied, such changes the kilo electron volts that are operating on the X-ray tube in order to develop the X-rays. Decalibration can also occur on occasion by variations in the power supply input to the unit.

Due to all of these various factors over which the operator has relatively little control, it is necessary to recalibrate these types of devices on a regular basis if accuracy is to be maintained. Calibration of these devices is deceptively simple. A standard that represents a relatively low fat content (for example about 20 percent) is inserted into the sample chamber of the device, and a low-fat calibration potentiometer is adjusted until a digital meter reads the value of the standard, such as 20 percent. Next, the low-fat standard is removed from the sample chamber, and a standard representing a high fat content is inserted thereinto (for example representing a 50 percent fat content), and a high-fat calibrating potentiometer is manually adjusted until the digital meter reads the value of the high-fat standard, such as 50 percent.

Complications arise because the two potentiometer adjustments interact with each other. That is, if the low-fat potentiometer had been set at a value that reads out as 20 percent fat, this value is changed when the other potentiometer is adjusted to give a 50 percent fat reading. Because of this, accurate calibration requires that the process of inserting and removing the pair of standards and adjusting the potentiometers must be repeated several times until no further adjustment is necessary. No further adjustment is necessary when the low-fat standard gives a reading identical to the low-fat standard value (such as 20 percent) and the high-fat standard gives a reading identical to the high-fat standard value (such as 50 percent) without requiring adjustment of either potentiometer so that a subsequent adjustment cannot cause the other potentiometer to move out of adjustment. At this stage, the device is calibrated. As decalibration occurs due to the various factors previously discussed, it is necessary to repeat this procedure. Unfortunately, many operators do not carefully follow this procedure, and their calibration is less than precise.

In many meat processing applications, a variety of meat species are processed from time to time. Typically, in prior art devices, it is necessary to recalibrate the device when changing from species to species, and it would be advantageous to include means that enable the operator to change the species being analyzed by the device without having to recalibrate same. For certain applications, it is desirable to ascertain not only the fat percentage of the meat being analyzed, but also the protein and moisture content thereof.

Accordingly, there is a need for a device that is capable of analyzing the fat content of a meat sample in a non-destructive and rapid manner which substantially eliminates the types of subjective operator involvement and possible operator error that are associated with the prior art devices. Further advantages would be realized, is such a device could be readily varied to account for different species and could also determine the protein and/or moisture content, as well as the fat content.

These various needs and advantages are capable of being attended to by the present invention, which includes automatic calibration to the extent that a pair of calibration standards are inserted into the device and X-ray radiation is transmitted thereto only once for each calibration operation, and the device accounts for the interaction between the individual calibration standards by passing digital outputs generated by the pair of calibration standards through a plurality of data channels. This automatic calibration feature includes the ability to shift, without recalibration, from one meat species to another meat species.

It is accordingly a general object of the present invention to provide improved non-destructive analysis of meat samples.

Another object of this invention is to provide automatic calibration of a device for determining the fat content of meat.

Another object of this invention is to provide an improved meat analysis device that may be particularly compact and portable.

Another object of the present invention is to provide an improved apparatus, method and system for determining the fat percentage of differing meat species without having to recalibrate each time a different species is analyzed.

Another object of the present invention is to provide improved analysis for determining the fat, moisture and protein content of meat, and for adjusting for high, normal or low moisture content of the meat being analyzed.

Another object of this invention is to provide for improved calibration of a meat analysis device that is both automatic and self-inhibiting relative to expected needed recalibration.

Another object of this invention is an improved meat analysis system that includes means for automatically ascertaining the stability of the X-ray signal.

These and other objects of the present invention will be apparent from the following detailed description, taken in conjunction with the accompanying drawings, wherein:

Figure 1:
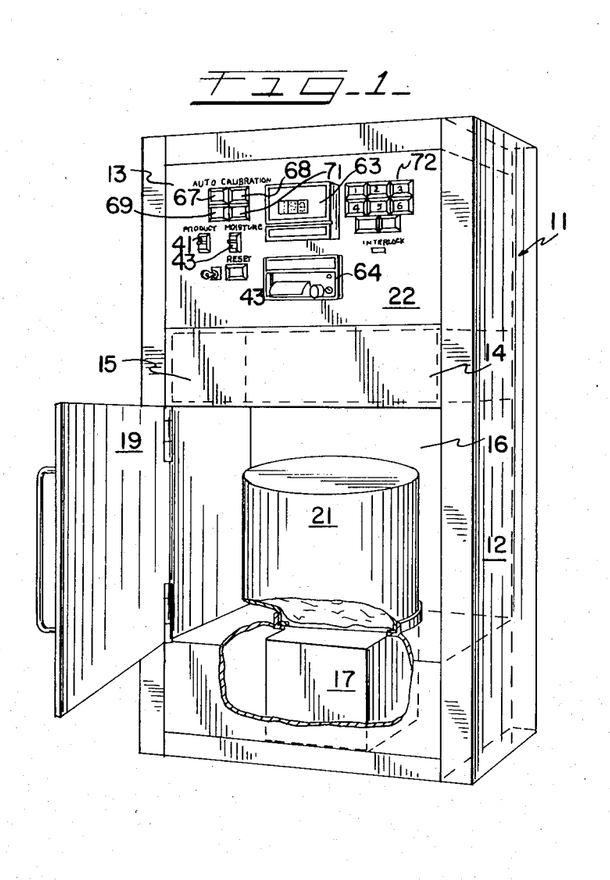
FIG. 1 is a perspective view illustrating the front portion of an apparatus according to this invention.
Figure 2:
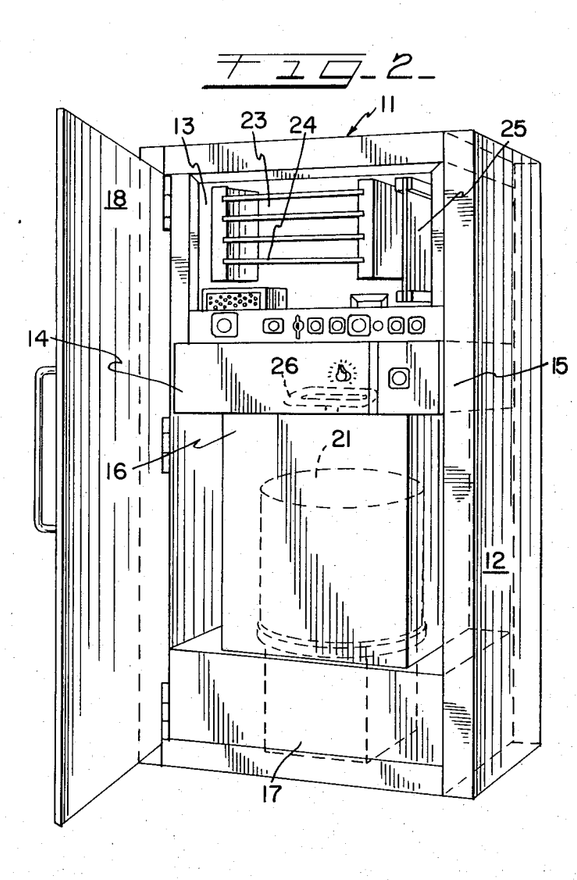
FIG. 2 is a perspective view illustrating the back portion of the apparatus illustrated in FIG. 1.

The meat analysis device according to this invention, generally designated as 11 in FIGS. 1 and 2, includes an outer, protective case 12, a control module 13, an X-ray module 14, a reference ion chamber 15, a sample chamber 16, and a sample ion chamber 17. The case 12 includes a large rear access door 18 and a front chamber door 19 through which a sample container 21 is inserted into the device 11.

Control module 13 includes a control panel 22, a data channel unit 23, an interface 24, and an X-ray control module 25. X-ray module 14 includes an X-ray tube 26 in which incident X-rays are generated and directed into the sample chamber 16 for passage through the sample container 21. When the X-ray beam passes through the sample container 21, it is attenuated, and the attenuated beam is received in the sample ion chamber 17. Additionally, a beam from the X-ray tube 26 is received by the reference ion chamber 15 in order to detect and measure the electron volts of the incident X-ray beam to thereby monitor the beam and account for possible variations therein.

Figure 3:
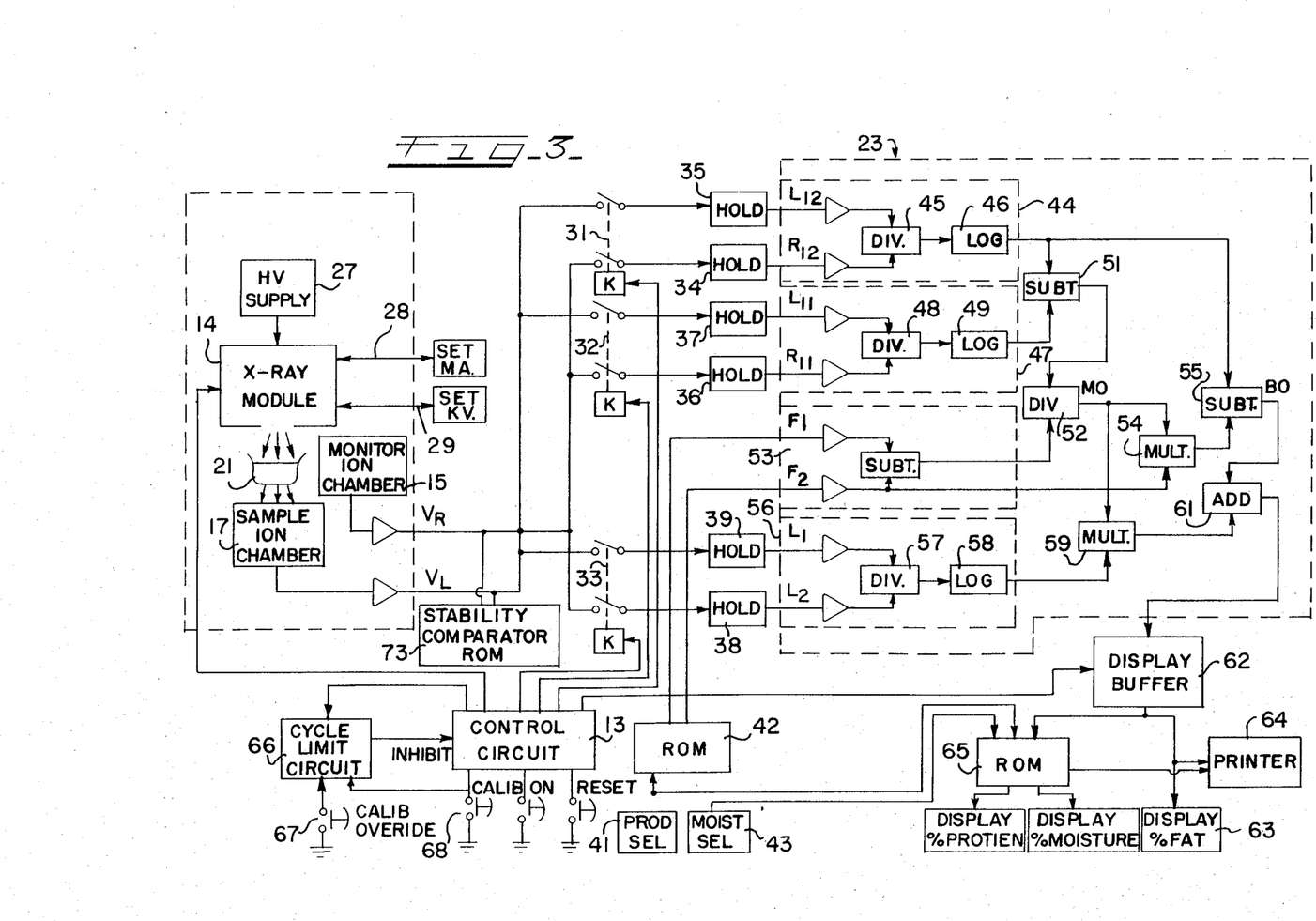
FIG. 3 is a simplified schematic diagram illustrating the various modules and channels of the apparatus according to this invention and the interaction among same.

With reference to FIG. 3, a high voltage supply 27 provides approximately 24 volts of DC current as the principal X-ray energy to the X-ray module 14. Parameters of the current for exciting the X-ray tube 26 are regulated by the X-ray control module 25. A self-compensatable feedback loop or circuit 28 monitors the current that is actually passing from the plate to the cathode of the X-ray tube 26. Another self-compensatable feedback loop or circuit 29 sets the amount of power supplied to the X-ray tube 26 in order to develop the desired plate voltage usually expressed in kilovolts, this circuit including means for varying resistance and for monitoring the plate voltage actually applied.

The x-ray beam that is monitored by the monitor ion chamber 15 generates a reference analog signal $V_R$, in order to monitor the incident beam generated by the X-ray tube 26. Radiation passing through the sample container 21 and to the sample ion chamber 17 develops a current in order to generate sample analog signal $V_L$. These analog signals are subsequently converted to digital signals and selectively submitted to sample and hold circuitry for controlled feed to the data channel assembly 23. More particularly, a plurality of relays, 31, 32 and 33, such as the double pole, single throw relays illustrated or the equivalents thereof are closed when activated by the control circuit 13, in preparation for passage of data to the data channel unit 23.

When the device 11 is in its calibrate mode, a known low-fat standard is inserted into the sample chamber 16 as the sample container 21, and the control circuit 13 activates the X-ray module 14 and the relay 31 such that the analog signal $V_R$ from the monitor ion chamber 15 is provided in digital form to sample and hold position 34. Also, analog symbol $V_L$ from sample ion chamber 17 is supplied in digital form to sample and hold position 35. Next, a high-fat standard is inserted into the sample chamber 16 as the sample container 21, and the control circuit 13 activates the X-ray module 14 and the relay 32, whereby the analog signal $V_R$ from the monitor ion chamber 15 is provided in digital form to the sample and hold position 36. The analog signal $V_L$ from the sample ion chamber 17 is provided in digital form to the sample and hold position 37.

A product selection assembly 41 provides address signals to the ROM 42 to thereby provide digital inputs $F_1$ and $F_2$ to the data channel unit 23. The particular inputs $F_1$ and $F_2$ are digital signals corresponding to the percent fat content of the low-fat standard and of the high-fat standard, respectively that are inserted during this calibration mode. These digital signals $F_1$ and $F_2$ differ depending upon the particular meat species being analyzed, for example, depending whether the species is beef, pork or mutton. By adjusting the product selection assembly, the digital signals $F_1$ and $F_2$ may be changed at any time, whether during the calibrate mode or the operate mode, whereby it is possible to easily change the meat sample from one species to another without having to recalibrate.

Typical pairs of calibration standards would include low-fat standard and high-fat standard pairs, such as a 20 percent–50 percent pair, a 10 percent–40 percent pair, a 10 percent–70 percent pair, a 30 percent–60 percent pair, or the like. Any such pair can be utilized during the calibration mode.

These $F_1$ and $F_2$ digital signals are systematically combined with digital input from the sample and hold positions 34, 35, 36 and 37 within the data channel unit 23. When thus combined, appropriate calibration signals are generated and stored to complete the calibration mode.

The device 11 is then in its operation mode, and the device 11 may provide a prompt to the effect that the device is calibrated and ready for unknown samples. An unknown sample is inserted into the sample container 21, and the control circuit 13 activates the X-ray module 14 and the relay 33 in order that the analog signal $V_R$ from the monitor ion chamber 15 is provided in digital form to signal and hold position 38, while the analog signal $V_L$ from the sample ion chamber 17 is provided in digital form to the sample and hold position 39. Data from the sample and hold positions 38 and 39 are input to the data channel unit 23, wherein they are appropriately combined with the calibration signals to eventually report the fat percentage of the unknown sample at the display 63.

As an optional aspect of this invention, a moisture selection assembly 43 provides address signals to the ROM 65 acting on signals from data from the unit 23. Each position of the moisture selection assembly 43 imparts a preselected digital factor the the data channel unit 23 for purposes of modifying the operations of ROM 65 depending upon the general moisture condition of the unknown meat sample being analyzed. If the particular unknown meat sample is from a source having a moisture content that is considered to be normal for the particular species of meat, than the factor imparted is the unitary factor. If the unknown sample is from a source that is believed to be at a generally low level of moisture, then the moisture selection assembly 43 provides address signals that reduce the magnitude of the operations performed on data from unit 23 by ROM 65 by a predetermined factor, such as by 0.2 thereof. If the unknown sample is from a source known to be high in moisture, then the moisture selection assembly 43 provides address signals that increase the magnitude of the operations performed on data from unit 23 by ROM 65 by a predetermined factor, such as by 0.2 thereof.

Digital signals from the supply and hold positions 34 through 39 and from the ROM 42 enter respective data channels of the data channel unit 23 with appropriate timing during the calibration mode and during the operation mode in order to achieve the necessary interaction therebetween as discussed hereinafter.

With reference to this aspect of the invention while the device 11 is in its calibration mode, digital signals $L_{12}$ and $R_{12}$ enter a first data channel 44 from respective supply and hold positions 35 and 34. The first data channel 44 includes a divider circuit 45, which divides the $L_{12}$ signal by the $R_{12}$ signal, and then a logging circuit 46 transforms the signal from the divider circuit 45 into its logarithmic equivalent to provide a first data channel output signal for passage to a first subtractor circuit 51 and to a second subtractor circuit 55.

A second data channel 47 receives the digital signals $L_{11}$ and $R_{11}$ from the respective supply and hold positions 37 and 36. The second data channel 47 includes a divider circuit 48 and a logging circut 49 for first dividing the $L_{11}$ signal by the $R_{11}$ signal and then transforming same into the logarithmic equivalent thereto to provide a second data channel output signal. The signal from the first data circuit 44 and the output signal from the second data circuit 47 are each passed to the first subtractor circuit 51 wherein the second data channel output signal is subtracted from the first data channel output signal and then input to a divider circuit 52.

In a third data channel 53, the digital signal $F_1$ is subtracted from the digital signal $F_2$, and the resulting difference signal is passed to the divider circuit 52, wherein the digital signal from the first subtractor circuit 51 is divided by the digital signal from the third digital channel 53 to thereby develop a calibration constant signal MO for the particular inputs from the high-fat standard and from the low-fat standard utilized, as well as the particular setting chosen for the product selection assembly 41 and, when included, the moisture selection assembly 43, each of said inputs being in accordance with the conditions of the overall device 11, including environmental influences upon it.

Substantially simultaneously, the $F_2$ input is passed to a first multiplier circuit 54, which also receives the MO signal from the divider circuit 52, after which a digital signal from the first multiplier circuit 54 passes to the second subtractor circuit 55, at which time this digital product signal is subtracted from the output signal from the first data channel 44. The resulting difference signal, a calibration constant signal BO, is a signal that is generated in view of the particular inputs provided by the high fat standard, by the low fat standard and by the particular choices on the product selection assembly 41. In this regard, each of the MO and BO signals are automatic calibration signals that are subsequently utilized to operate upon signals imparted to the data channel unit 23 by a meat sample to unknown fat percentage when the device 11 is in its operate mode.

Referring more particularly to the operate mode, a meat sample of unknown fat percentage is inserted into the sample container 21. The control circuit 13 is turned on in order to energize the X-ray module 14 and the relay 33. The analog signal $V_R$ from the monitor ion chamber 15 and the analog signal $V_L$ from the sample ion chamber 17 are transformed to respective digital signals that may be stored at sample and hold positions 38 and 39, respectively. Digital signal $L_1$ from the sample and hold position 39 and digital signal $R_1$ from the sample and hold position 38 are input to a fourth data channel 56, wherein the $L_1$ input is divided by the $R_1$ input in a divider circuit 57. Output from the divider circuit 57 is operated on by a logging circuit 58 to provide digital input for a second multiplier circuit 59.

Also input to the second multiplier circuit 59 is the MO signal from the divider circuit 52. Then, the product signal output from the second multiplier circuit 59 is passed to an adder circuit 61. Within adder circuit 61, the output signal from the second multiplier circuit 59 is summed with the BO signal output from the second subtractor circuit 55, and the resulting sum is passed to a display buffer 62 which converts the signal from the adder circuit 61 to a signal that is compatible with subsequent circuitry, including a percent fat display 63, which may be a liquid crystal display or other suitable display arrangement. Alternatively, this signal may be imparted to a suitable printer 64, or it may be imparted to both a display 63 and a printer 64, optionally in association with a print data switch 69 (FIG. 1).

An optional feature of the device 11 is one wherein the percent protein and percent moisture are determined and displayed in addition to the percent fat of the particular unknown sample. According to this aspect of the invention, input from the data channel unit 23 eventually passes to the ROM 65. ROM 65 operates on these inputs in a manner that is determined by empirically generated moisture/protein ratios. Typical additional input to the ROM 65 can be from the product selection assembly 41 and from the moisture selection assembly 43. This aspect of the invention recognizes the fact that it is not possible to directly convert from a percent fat to a percent moisture and/or to a percent protein, since the interrelationship among fat, moisture and protein percent is dependent upon many factors, including the age and species of the animal, and variables such as methods of feeding, reason for slaughter, and the like, which factors can be adjusted for by the moisture selection assembly 43. Such is accomplished by circuitry that operates on input to the ROM 65 in a manner that is consistent with moisture/protein ratios which are statistically determined according to empirical data that are typically industry-wide.

While the device 11 is in its calibrate mode, and before being needed for the operate mode, the MO signal and the BO signal are stored within the data channel unit 23. For example, the MO signal may be stored in the second multiplier circuit 59, and the BO signal may be stored in the adder circuit 61.

A cycle limit circuit 66 may be provided which interfaces with the control circuit 13 to the extent that, after a predetermined number of unknown samples have been analyzed by the device 11, the cycle limit circuit 66 imparts an inhibit signal to the control circuit 13, which inhibit signal takes the device 11 out of the operate mode and into the calibrate mode. As a result, the device 11 must be recalibrated before further samples can be run unless a calibration override switch 67 is activated. If, at any time, it is desired to recalibrate the device 11 before the cycle limit circuit 66 imparts an inhibit signal, the calibrate switch 68 on the control circuit 13 can be activated in order to take the device 11 out of the operate mode and into the calibrate mode.

Provided is an array 72 having a plurality of X-ray initiate switches, each of which initiate the circuitry to perform substantially the same functions except that each prints a different product code number, for example numbers 1 through 5 as illustrated in FIG. 1. An unnumbered button in array 72 provides an output report that is of shortened format, for example reporting only percentage fat, sample number, species, data and time. This saves operation time when compared with reporting functions provided when one of the other switches of the array 72 is activated, to initiate the development and report of the data of the shortened format plus the particular product code designated by the switch and, when ROM 65 and its associated circuitry are included, the percent protein, the percent moisture and the moisture/protein ratio.

When desired, a print data mode may be activated by depressing the print data button 69. When this mode is activated while the device 11 is in the operate mode, the reported data can include date, time, sample number, species, percent fat, $R_1$, $L_1$, KV, the fat percentage of each sample previously run, and the average fat percent thereof. Typically, after the print data switch is activated, the data memory bank can be erased and subsequent data stored in its place. Suitable circuitry can be provided in order to report the date and time only by activating the print date/time switch 71 (FIG. 1).

If the print data mode is activated while the device 11 is fully calibrated but still in the calibrate mode, the data that is reported when the print data button 69 is activated include BO, MO, $R_{12}$, $L_{12}$, $R_{11}$, $L_{11}$ and KV, which information can be particularly useful for trouble-shooting purposes.

Prompting signals may be provided. For example, during the calibration mode, the operator can be prompted to insert a low-fat standard and then a high-fat standard. If one of the insertions is omitted, a "calibration data missing" prompt is provided. During calibration, should a high-fat standard or a low-fat standard be inserted which is in error, appropriate circuitry may be provided to compare the $V_L$ input, when converted to digital form, with expected ranges and to print a prompt such as "error/out of range".

Appropriate data channels may be provided as a check on the stability of an ion chamber signal input. Should the check indicate a deviation beyond a predetermined level, an appropriate prompt is provided such as "unstable signals—data may be in error". A stability comparator ROM circuit 73 is provided for this purpose whereby, when any particular meat sample is within the sample container 21 and when the device is in its operate mode, the stability comparator circuit 73 receives and stores separate inputs from the ion chamber for a given number of consecutive times, for example three times. The stability comparator ROM 73 includes circuitry for summing and averaging each of these stored sample signals to determine the average sample signal value. If this average value deviates from any one of the individually measured and stored sample signal values by a predetermined amount, for example one percent, then the stability of the signal is less than desired. Preferably, the stability comparator 73 then repeats this procedure with three different consecutive sample signals, and this process may be repeated again until either the deviation is less than the predetermined amount, or until the predetermined number of readings have been input and processed by the stability comparator 73. If the deviation remains greater than the predetermined amount, the prompt may be accompanied by an appropriate inhibit signal to shut down the control circuit 13.

Rather than providing the circuitry and the individual data channels described herein and illustrated diagrammatically, the operations performed by these channels and circuits can be implemented in and performed by a suitably programmed digital computer of any known construction, including a microprocessor.

While a particular embodiment of the invention has been described, it will be apparent to those skilled in the art that various modifications thereof may be made without departing from the true spirit and scope of the invention. Accordingly, it is intended by the appended claims to cover all such modifications and equivalents which embody the inventive features as defined in the claims.

What is claimed is:

1. A system for analyzing the quantitative relationship of components of meat, such as the weight percent of fat thereof, comprising:
   means for serially transmitting a first, second and third incident beam of X-ray radiation respectively through a first calibration standard, a second calibration standard and an unknown sample, for respectively absorbing a portion of the radiation by the first calibration standard, the second calibration standard and the unknown sample;

means for serially detecting the radiation respectively not absorbed by the first calibration standard, the second calibration standard and the unknown sample, and for converting the respective detected radiation to a first calibration digital electrical signal, a second calibration digital signal and an unknown sample digital signal;

means for monitoring the intensity of the incident beam and for converting the resulting incident beam monitor signal to a monitor digital electrical signal;

first data channel circuit means for operating on said first calibration digital electrical signal and on said monitor digital electrical signal to provide a first data channel output;

second data channel circuit means for operating on said second calibration digital electrical signal and on said monitor digital electrical signal to provide a second data channel output;

third data channel circuit means for operating on a pair of signals corresponding to known component quantities of said first calibration standard and of said second calibration standard to provide a third data channel output;

combination data circuit means for operating on the first data channel output, the second data channel output, the third data channel output and one of the pair of signals corresponding to known component quantities of the calibration standards in order to develop calibration constant digital signals, whereby the various circuitry of the system is generally positioned for transition of the system from its calibrate mode to its operate mode;

fourth data channel circuit means for operating on said unknown sample digital signal and on said monitor digital electrical signal to provide a fourth data channel output;

unknown sample data channel circuit means for operating on said fourth data channel output and on said calibration constant digital signals in order to provide a resultant digital signal; and means for displaying said resultant signal as a component weight percent of the unknown sample being analyzed.

2. The system of claim 1, wherein said means for monitoring the intensity of the incident beam proceeds with such determination on a serial basis at each respective time that the first, second and third incident beams are transmitted.

3. The system of claim 1, wherein said combustion data circuit means operates on said first, second and third data channel outputs to develop a first calibration constant digital signal, and said combination data circuit further operates on said first, second and third data channel outputs and on one of the signals corresponding to a known component quantity of the calibration standards to develop a second calibration constant digital signal.

4. The system of claim 1, wherein said first, second and third data channel circuit means each include a divider circuit and a logging circuit.

5. The system of claim 1, wherein said third data channel circuit means includes a subtractor circuit.

6. The system of claim 1, wherein said combination data circuit means includes a first subtractor circuit that operates on said first and second data channel outputs for providing a first difference digital signal, said combination data circuit means further including a divider circuit that operates on said first difference digital signal and said third data channel output for providing a first calibration constant digital signal.

7. The system of claim 1, wherein said combination data circuit means includes a first multiplier circuit that operates on a first one of said calibration constant digital signals and on said one of the pair of signals corresponding to known component quantities of the calibration standards in order to develop a first product digital signal, said combination data circuit means further including a second subtractor circuit that operates on said first product digital signal and on said first data channel output for providing a second calibration constant digital signal.

8. The syste of claim 1, wherein said unknown sample data channel circuit means includes a second multiplier circuit and an adder circuit.

9. The system of claim 1, wherein said combination data circuit means includes a first subtractor circuit that operates on said first and second data channel outputs for providing a first difference digital signal, said combination data circuit means further including a divider circuit that operates on said first difference digital signal and said third data channel output for providing a first calibration constant digital signal wherein said combination data circuit means also includes a first multiplier circuit that operates on a first one of said calibration constant digital signals and on said one of the pair of signals corresponding to known component quantities of the calibration standards in order to develop a first product digital signal, said combination data circuit means further including a second subtractor circuit that operates on said first product digital signal and on said first data channel output for providing a second calibration constant digital signal, and wherein said unknown data channel circuit means includes a second multiplier circuit that operates on said first calibration constant digital signal and on said fourth data channel output in order to provide a second product digital signal, said unknown data channel circuit further including an adder circuit for operating on said second calibration constant digital signal and on said second product digital signal to provide said resultant digital signal.

10. The system of claim 1, further including a ROM and a product selection assembly for address signalling said ROM to provide said pair of signals to said third data channel circuit means.

11. The system of claim 1, further including a ROM and a product selection assembly for address signalling said ROM to provide said pair of signals so addressed to said third data channel circuit means.

12. The system of claim 1, further including a ROM for receiving the resultant digital signal, said ROM including fat/moisture/protein ratio circuitry that is keyed to said resultant digital signal, and said displaying means displays the fat, moisture and protein percentage of the unknown sample being analyzed.

13. The system of claim 12, further including a product selection assembly to provide address signals to said ROM, and said fat/moisture/protein ratio circuitry is further keyed by said product selection address signals.

14. The system of claim 1, further including a cycle limit circuit that provides an inhibit impulse to automatically take the system out of its operate mode and into its calibrate mode.

15. The system of claim 1, further including circuitry for displaying a first prompt to insert said first calibration standard in an X-ray radiation receiving orientation with respect to said transmitting means and then for displaying a second prompt to insert said second calibration standard in said X-ray radiation receiving orientation, said circuitry being such that the second prompt is displayed only after said first prompt has been displayed and said X-ray radiation transmitting means has been activated.

16. The system of claim 1, further including a stability comparator circuit including a ROM for reading a series of radiation signals from said X-ray radiation transmitting means, said stability comparator ROM including circuitry for summing and averaging said series of radiation signals and for storing a resultant average radiation signal, said ROM further including circuitry for comparing and determining the deviation between each radiation signal with respect to said average radiation signal, said system further including prompt means for reporting when any such deviation is greater than a predetermined value.

17. A system for analyzing the quantitative relationship of components of meat, such as the weight percent of fat thereof, comprising:
  means for transmitting a first incident beam of X-ray radiation through a first calibration standard for absorbing a portion of the radiation by the first calibration standard;
  means for detecting the radiation not absorbed by the first calibration standard and for converting the detected radiation to a first calibration digital electrical signal;
  means for monitoring the intensity of the first incident beam of radiation at the time same is transmitted through the first calibration standard and for converting the resulting first incident beam monitor signal to a monitor digital electrical signal;
  first data channel circuit means for operating on a first pair of signals to provide a first data channel output, said first pair of signals being said first calibration digital signal and said first monitor digital signal;
  means for transmitting a second incident beam of X-ray radiation through a second calibration standard for absorbing a portion of the radiation by the second calibration standard;
  means for detecting the radiation not absorbed by the second calibration standard and for converting the detected radiation to a second calibration digital electrical signal;
  means for monitoring the intensity of the second incident beam of radiation at the time same is transmitted through a second calibration standard and for converting the resulting second incident beam monitor signal to a monitor digital electrical signal;
  second data channel circuit means for operating on a second pair of signals to provide a second data channel output, said second pair of signals being said second calibration digital signals and said second monitor digital signal;
  third data channel circuit means for operating on a third pair of signals corresponding to known coponent quantities of said first calibration standard and of said second calibration standard, respectively, to provide a third data channel output;
  combination data channel circuit means for operating on the first data channel output, the second data channel output and the third data channel output to develop a digital signal representing a first calibration constant, said combination data channel circuit means further being for operating on the first data channel output, the second data channel output, the third data channel output, and one of said pair of digital inputs corresponding to known component quantities of the calibration standards in order to develop a digital signal representing a second calibration constant;
  means for transmitting a third incident beam of X-ray radiation through an unknown meat sample for absorbing a portion of the radiation by the unknown meat sample;
  means for detecting the radiation not absorbed by the unknown meat sample and for converting the detected radiation to an unknown sample digital electrical signal;
  means for monitoring the intensity of the third incident beam of radiation at the time same is transmitted through the unknown meat sample and for converting the resulting third incident beam monitor signal to a monitor digital electrical signal;
  fourth data channel circuit means for operating on a fourth pair of signals to provide a fourth data channel output, said fourth pair of signals being said unknown sample digital electrical signal and said third monitor digital signal;
  unknown sample data channel circuit means for operating on said fourth data channel output and on said first and second calibration constants of the combination data channel circuit means in order to provide a resultant digital signal; and
  means for displaying said resultant signal as a component weight percent of the unknown sample being analyzed.

18. The system of claim 17, wherein said first, second and fourth data channel circuit means each include a divider circuit and a logging circuit.

19. The system of claim 17, wherein said third data channel circuit means includes a subtractor circuit.

20. The system of claim 17, wherein said combination data channel circuit means to develop the first calibration constant digital signal includes a first subtractor circuit and a divider circuit.

21. The system of claim 17, wherein said combination data channel circuit means to develop the second calibration constant digital signal includes a first multiplier circuit and a second subtractor circuit.

22. The system of claim 17, wherein said unknown sample data channel circuit means includes a second multiplier circuit and an adder circuit.

23. The system of claim 17, further including a ROM and a product selection assembly for address signalling said ROM to provide said pair of signals so addressed to said third data channel circuit means.

24. The system of claim 17, further including a ROM for receiving the resultant digital signal, said ROM including fat/moisture/protein ratio circuitry that is keyed to said resultant digital signal and to a product selection signal from a product selection assembly, the system further including a moisture selection assembly for imparting a moisture factor signal to said ROM.

25. A method for automatically calibrating a system for analyzing the quantitative relationship of components of meat, such as the weight percent of fat thereof, comprising:

- transmitting an incident beam of X-ray radiation through a first calibration standard for absorbing a portion of the radiation by the first calibration standard;
- detecting the radiation not absorbed by the first calibration standard and converting the detected radiation to a digital electrical signal;
- monitoring the intensity of the incident beam of radiation when same is transmitted through the first calibration standard and converting the resultant incident beam monitor signal to a monitor digital electrical signal;
- passing said first calibration detected radiation electrical signal and said first monitor electrical signal as a pair of signals to a first data channel, and operating on said pair of signals in said first data channel to provide a first data channel output;
- transmitting an incident beam of X-ray radiation through a second calibration standard for absorbing a portion of the radiation by the second calibration standard;
- detecting the radiation not absorbed by the second calibration standard and converting the detected radiation to a digital electrical signal;
- monitoring the intensity of the incident beam of radiation when same is transmitted through the second calibration standard and converting the resultant second incident beam monitor system to a monitor digital electrical signal;
- passing said second calibration detected radiation electrical signal and said second monitor electrical signal as a pair of signals to a second data channel and operating on said pair of signals in said second data channel to provide a second data channel output;
- providing a pair of digital inputs corresponding to known component quantities of said first calibration standard and of said second calibration standard, respectively;
- passing said pair of digital inputs corresponding to known quantities to a third data channel and operating on said pair of signals in said third data channel to provide a third data channel output;
- subtracting the second data channel output from the first data channel output and dividing the resulting difference by the third data channel output to develop a digital signal representing a first calibration constant;
- inputting the digital input corresponding to the known component quantity of one of the calibration standards to a multiplier circuit, and inputting the first calibration constant signal to said multiplier circuit for developing a product output; and
- passing said product output to a subtractor circuit and passing said first data channel output to said subtractor circuit, and operating on the input to said subtractor circuit to develop a digital signal representing a second calibration constant.

26. The calibrating method of claim 25, wherein said operating steps of the first and second data channels each include a dividing step and a logging step.

27. The calibrating method of claim 25, wherein said oprating of the third data channel includes a subtracting step.

28. The calibrating method of claim 25, wherein said operating of the third data channel includes operating on a signal corresponding to a selection of the species of the meat to be analyzed.

29. A method for analyzing the quantitative relationship of components of meat, such as the weight percent of fat thereof, comprising:

- serially transmitting a first and second incident beam of X-ray radiation respectively through a first calibration standard and a second calibration standard, and respectively absorbing a portion of the radiation by the first calibration standard and by the second calibration standard;
- serially detecting the radiation respectively not absorbed by the first calibration standard and by the second calibration standard, and converting the respective detected radiation to a first calibration digital electrical signal and a second calibration digital signal;
- monitoring the intensity of the incident beam and converting the resultant incident beam monitor signal to a monitor electrical signal;
- operating on said first calibration digital electrical signal and on said monitor digital electrical signal to provide a first data channel output;
- operating on said second calibration digital electrical signal and on said monitor digital electrical signal to provide a second data channel output;
- operating on a pair of signals corresponding to known component quantities of said first calibration standard and of said second calibration standard to provide a third data channel output;
- combining the first data channel output, the second data channel output, the third data channel output and one of the pair of signals corresponding to known component quantities of the calibration standards, and developing calibration constant digital signals during a calibrate mode;
- initiating an operate mode by transmitting an incident beam of X-ray radiation through an unknown meat sample and absorbing a portion of the radiation by the unknown sample;
- detecting the radiation not absorbed by the unknown sample and converting the detected radiation to an unknown sample digital signal;
- operating on said unknown sample digital signal and on said monitor digital electrical signal to provide a fourth data channel output;
- operating on said fourth data channel output and on said calibration constant digital signals in order to provide a resultant digital signal; and
- displaying said resultant signal as a component weight percent of the unknown meat sample being analyzed.

30. The analyzing method of claim 29, wherein said operating steps to provide the first, second and fourth data channel outputs each include a dividing step and a logging step.

31. The analyzing method of claim 29, wherein said operating step to provide the third data channel output includes a subtracting step.

32. The analyzing method of claim 29, wherein said operating of the third data channel includes operating on a signal corresponding to a selection of the species of the meat to be analyzed.

* * * * *

UNITED STATES PATENT AND TRADEMARK OFFICE
CERTIFICATE OF CORRECTION

PATENT NO. : 4,504,963
DATED : March 12, 1985
INVENTOR(S) : Lloyd D. Johnson

It is certified that error appears in the above—identified patent and that said Letters Patent is hereby corrected as shown below:

Column 3, line 4, "is" should read --if--.
Column 8, lines 49 and 50, "digrammatically" should read --diagrammatically--.
Column 9, line 55, "combustion" should read --combination--.
Column 10, line 20, "syste" should read --system--.
Column 11, lines 65 and 66, "coponent" should read --component--.
Column 13, line 65, "oprating" should read --operating--.

Signed and Sealed this

Nineteenth Day of November 1985

[SEAL]

Attest:

DONALD J. QUIGG

Attesting Officer

*Commissioner of Patents and Trademarks*